(12) United States Patent
Levy

(10) Patent No.: US 12,409,271 B2
(45) Date of Patent: Sep. 9, 2025

(54) APPARATUS AND METHOD FOR PRODUCING AN ENRICHED MEDICAL SUSPENSION

(71) Applicant: Frank Levy, Fort Myers, FL (US)

(72) Inventor: Frank Levy, Fort Myers, FL (US)

(*) Notice: Subject to any disclaimer, the term of this patent is extended or adjusted under 35 U.S.C. 154(b) by 705 days.

(21) Appl. No.: 17/660,514

(22) Filed: Apr. 25, 2022

(65) Prior Publication Data

US 2023/0338658 A1    Oct. 26, 2023

(51) Int. Cl.
| | | |
|---|---|---|
| *A61M 5/19* | (2006.01) | |
| *A61M 11/00* | (2006.01) | |
| *A61M 25/00* | (2006.01) | |
| *A61M 5/178* | (2006.01) | |

(52) U.S. Cl.
CPC ............ *A61M 5/19* (2013.01); *A61M 11/007* (2014.02); *A61M 25/0026* (2013.01); *A61M 25/003* (2013.01); *A61M 25/0068* (2013.01); *A61M 25/007* (2013.01); *A61M 25/0071* (2013.01); *A61M 2005/1787* (2013.01); *A61M 2025/0034* (2013.01); *A61M 2025/0073* (2013.01); *A61M 2202/04* (2013.01); *A61M 2209/082* (2013.01)

(58) Field of Classification Search
CPC .................. A61M 5/19; A61M 11/007; A61M 2005/1787; A61B 2017/00495; A61J 1/20; A61J 1/2093

See application file for complete search history.

(56) References Cited

U.S. PATENT DOCUMENTS

| | | |
|---|---|---|
| 3,831,844 A | 8/1974 | Tropeano et al. |
| 4,044,757 A * | 8/1977 | McWhorter ........ A61M 5/1456 604/82 |
| 4,219,021 A | 8/1980 | Fink |
| 5,154,348 A | 10/1992 | Ratnik et al. |
| 5,195,963 A | 3/1993 | Yafuso et al. |
| 5,345,932 A | 9/1994 | Yafuso et al. |
| 5,395,318 A | 3/1995 | Kaprelian |
| 5,580,530 A | 12/1996 | Kowatsch et al. |
| 5,699,961 A | 12/1997 | Ratnik et al. |
| 5,875,776 A | 3/1999 | Vaghefi |
| 5,964,223 A | 10/1999 | Baran |
| 6,164,556 A | 12/2000 | Dupre et al. |
| 6,402,047 B1 | 6/2002 | Thomas |
| 6,474,091 B2 | 11/2002 | Guerra |
| 6,572,873 B1 | 6/2003 | Osman et al. |
| 6,610,033 B1 | 8/2003 | Melanson |

(Continued)

FOREIGN PATENT DOCUMENTS

| | | |
|---|---|---|
| EP | 246820481 A1 | 6/2012 |
| EP | 2548607 A2 | 1/2013 |

(Continued)

*Primary Examiner* — Wesley G Harris
(74) *Attorney, Agent, or Firm* — Welsh Flaxman & Gitler LLC

(57) ABSTRACT

A medical fluid suspension generating delivery apparatus includes a dual syringe assembly including a first receptacle for a pressurized chemical solution and a second receptacle for a medical solution. The medical fluid suspension generating delivery apparatus also includes a Venturi-agitating tip assembly generating an enriched medical suspension from the pressurized chemical solution and a second receptacle for a medical solution.

8 Claims, 13 Drawing Sheets

(56) References Cited

U.S. PATENT DOCUMENTS

Figure 1:
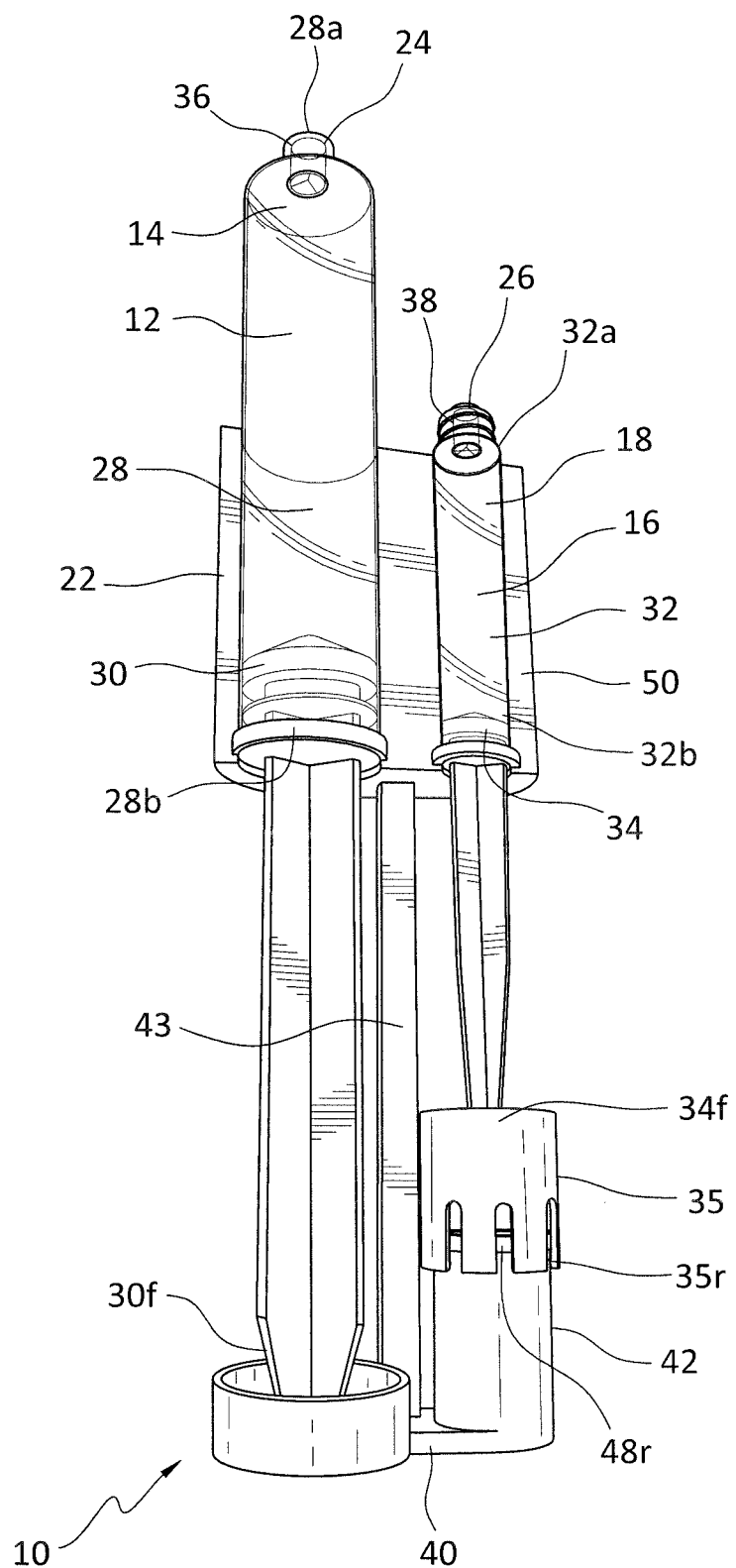
Figure 2:
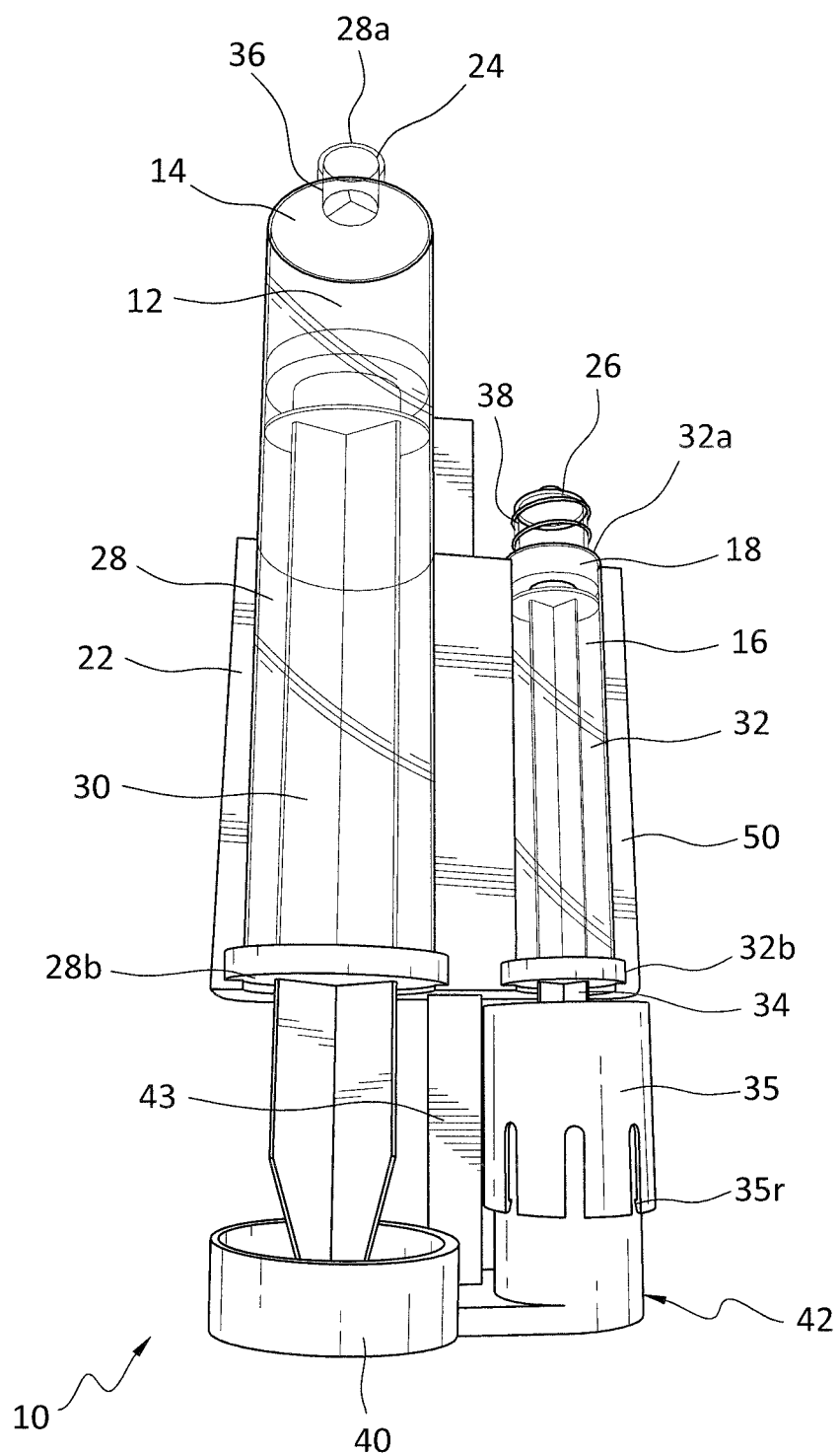
Figure 3:
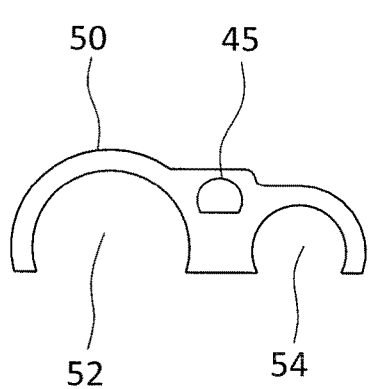
Figure 4:
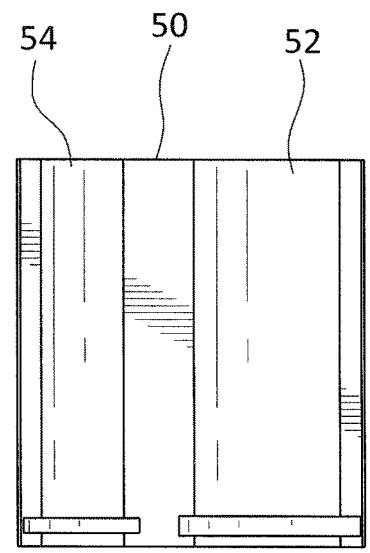
Figure 5:
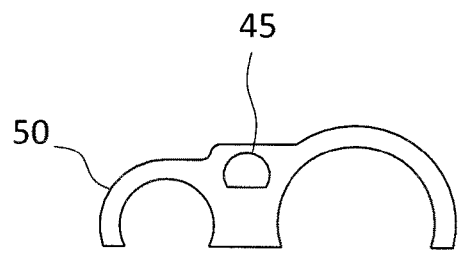
Figure 6:
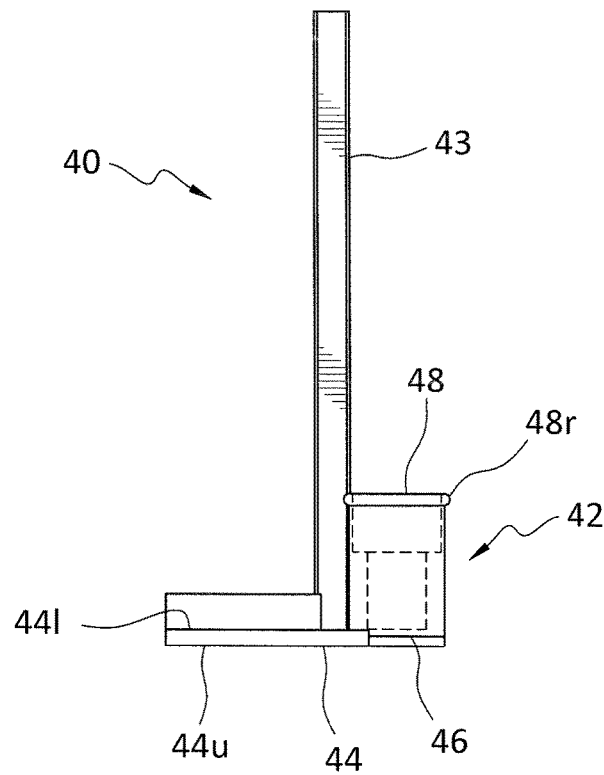

| | | | |
|---|---|---|---|
| 6,939,329 B1 * | 9/2005 | Verkaart | A61M 5/19 604/82 |
| 6,959,708 B1 | 11/2005 | Rasor et al. | |
| 7,543,760 B2 | 6/2009 | Levy et al. | |
| 7,763,269 B2 | 7/2010 | Wright et al. | |
| 8,876,749 B2 | 11/2014 | Levy | |
| 9,744,342 B2 | 8/2017 | Levy | |
| 10,155,093 B2 | 12/2018 | Levy et al. | |
| 10,322,271 B2 | 6/2019 | Levy et al. | |
| 10,350,398 B2 | 7/2019 | Levy | |
| 10,350,399 B2 | 7/2019 | Levy et al. | |
| 2002/0174578 A1 | 11/2002 | Ross | |
| 2006/0071091 A1 | 4/2006 | Ratnik | |
| 2006/0074386 A1 | 4/2006 | Wollmann et al. | |
| 2006/0178620 A1 | 8/2006 | Wollmann et al. | |
| 2006/0253082 A1 * | 11/2006 | McIntosh | A61M 5/19 604/82 |
| 2007/0104651 A1 | 5/2007 | Wright et al. | |
| 2007/0244429 A1 | 10/2007 | Nguyen et al. | |
| 2008/0120992 A1 | 5/2008 | Levy et al. | |
| 2008/0167621 A1 * | 7/2008 | Wagner | A61M 5/19 600/432 |
| 2009/0062741 A1 | 3/2009 | Smith et al. | |
| 2009/0194453 A1 | 8/2009 | Thorne | |
| 2009/0198211 A1 * | 8/2009 | Thorne, Jr. | A61M 5/002 604/533 |
| 2009/0198217 A1 | 8/2009 | Thorne | |
| 2009/0264831 A1 * | 10/2009 | Thompson | A61B 17/00491 604/191 |
| 2009/0318890 A1 | 12/2009 | Levy | |
| 2010/0101579 A1 | 4/2010 | Levy | |
| 2011/0106054 A1 * | 5/2011 | Osborne | A61M 5/31581 604/82 |
| 2011/0245866 A1 | 10/2011 | Cassingham | |
| 2014/0148791 A1 | 5/2014 | Neomend | |
| 2014/0257179 A1 * | 9/2014 | Schwab | A61M 5/31596 604/82 |
| 2015/0133779 A1 | 5/2015 | Yurek | |
| 2016/0166782 A1 * | 6/2016 | Levy | A61B 17/12109 604/507 |
| 2017/0035653 A1 * | 2/2017 | Osborne | B01F 25/4314 |
| 2019/0307971 A1 | 10/2019 | Levy | |

FOREIGN PATENT DOCUMENTS

| | | | | |
|---|---|---|---|---|
| ES | 2332032 A1 * | 1/2010 | | A61B 17/00491 |
| JP | 2000262525 A * | 9/2000 | | A61M 5/19 |
| WO | 9300951 A1 | 1/1993 | | |
| WO | 0072821 A1 | 12/2000 | | |
| WO | 0241872 A1 | 5/2002 | | |
| WO | 2005048984 A1 | 6/2005 | | |

* cited by examiner

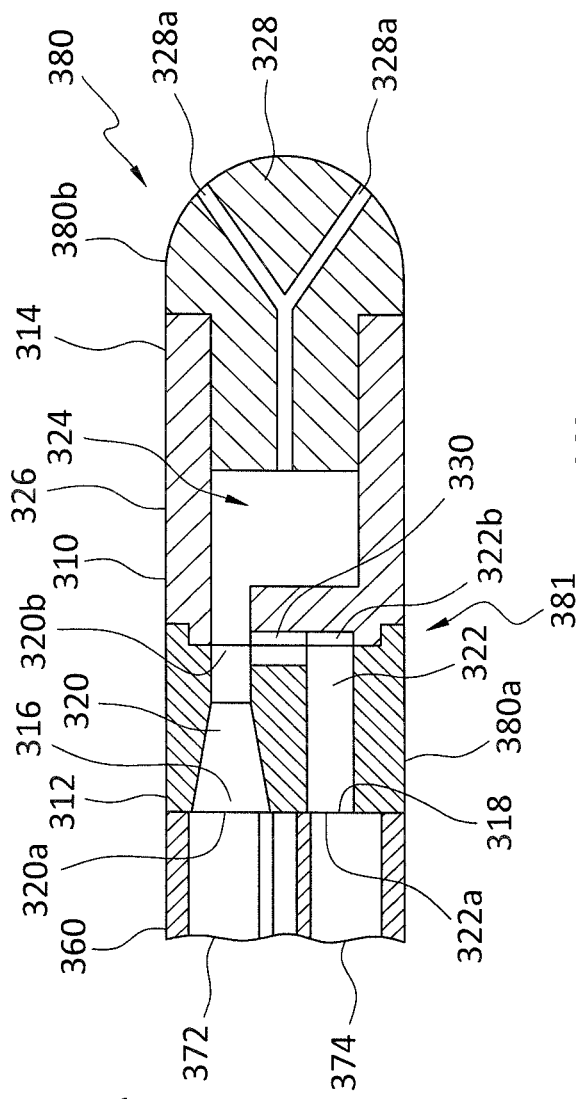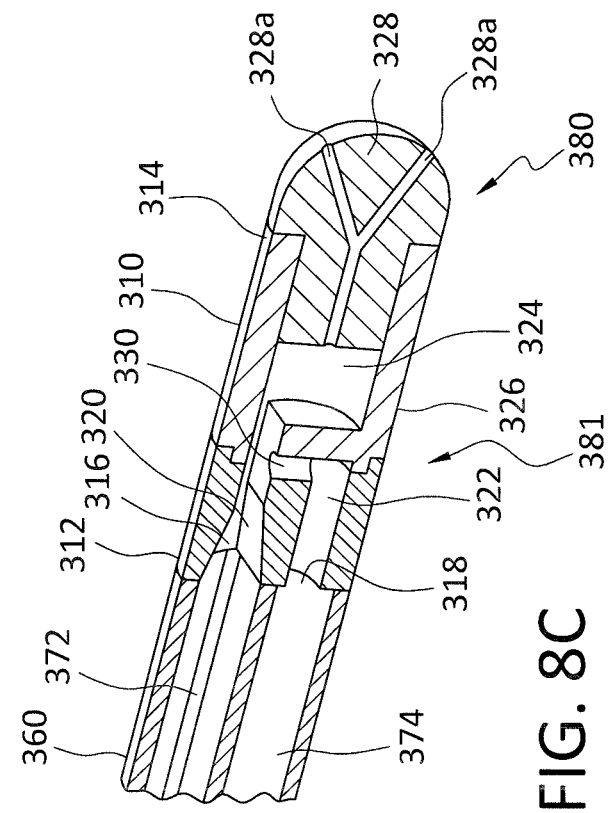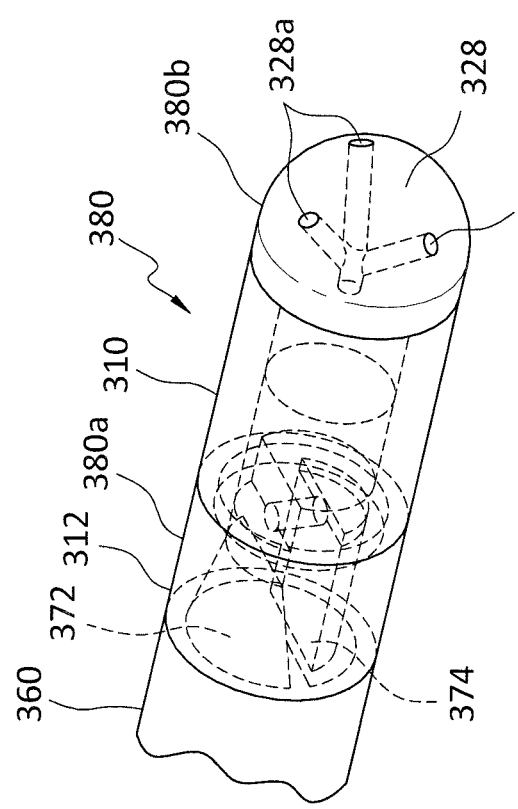

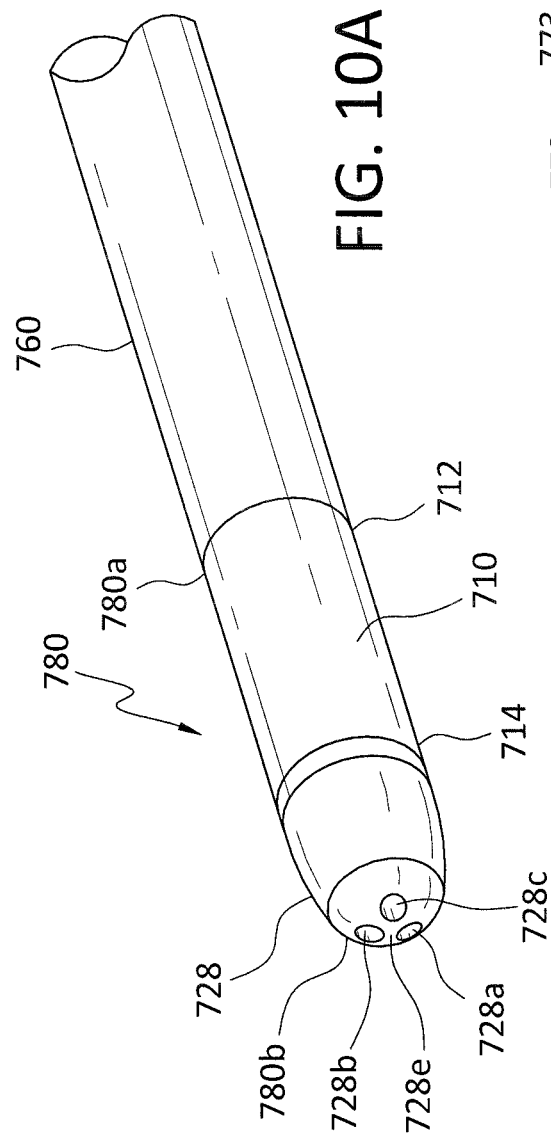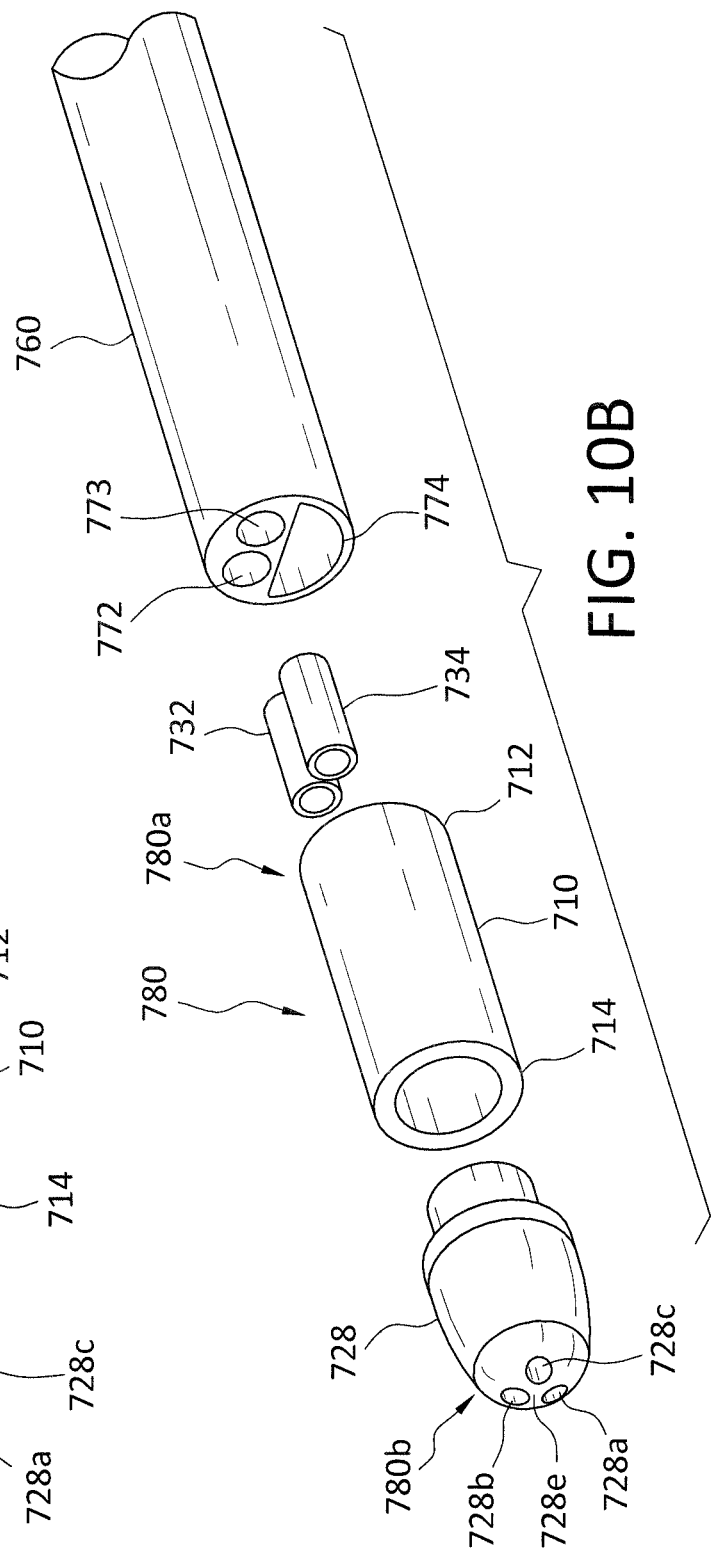

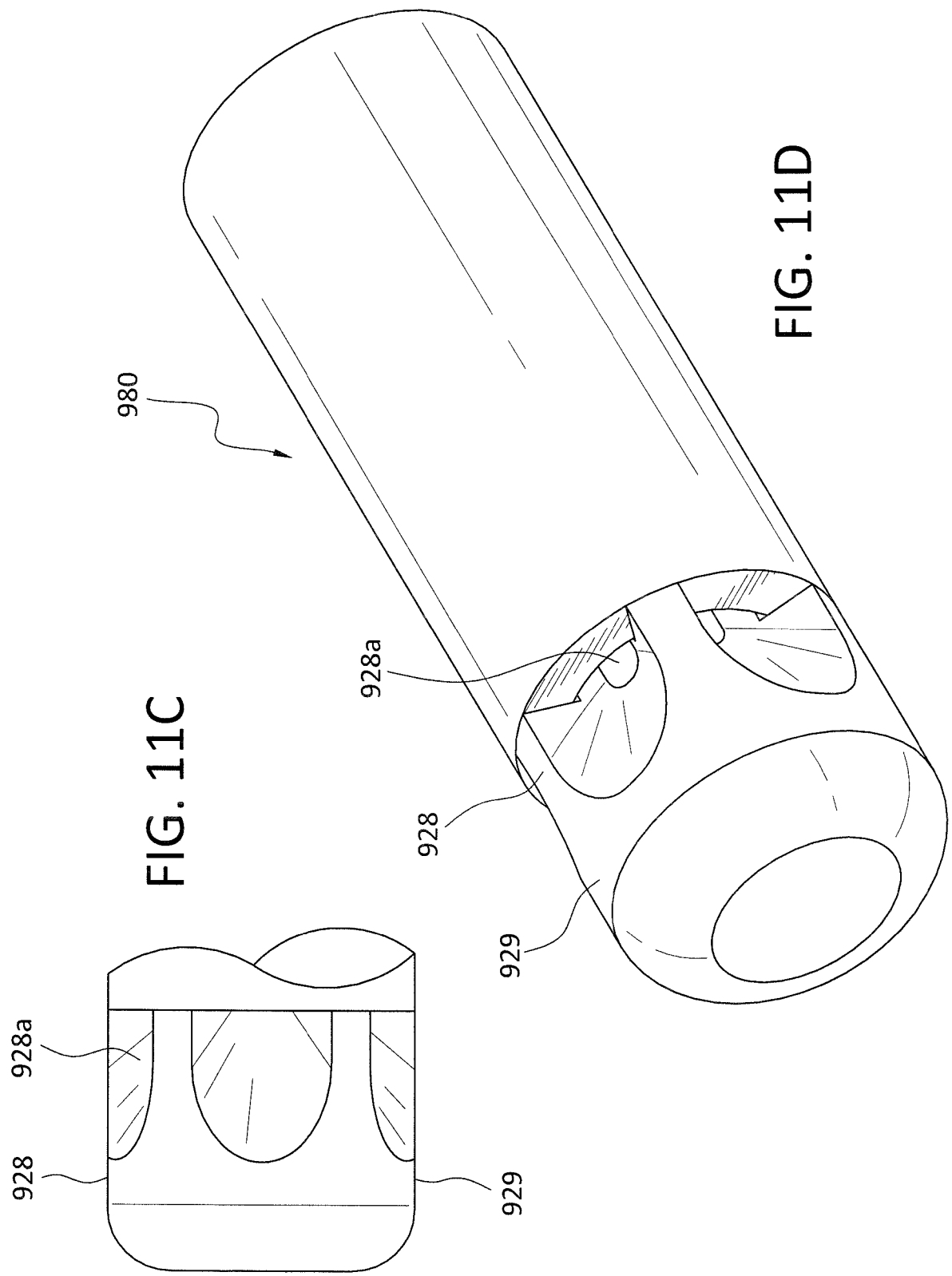

APPARATUS AND METHOD FOR PRODUCING AN ENRICHED MEDICAL SUSPENSION

BACKGROUND OF THE INVENTION

Field of the Invention

This invention relates to an apparatus for producing an enriched medical suspension.

Description of Related Art

The present invention utilizes the Venturi effect to produce an enriched medical suspension for use in various applications. The apparatus of the present invention is simple to manufacture and use because it does not require an impeller and incorporated fan in order to create and dispense the enriched medical suspension.

The Venturi effect is an example of Bernoulli's principle, in the case of incompressible fluid, flow through a tube or pipe with a constriction in it. The fluid velocity must increase through the constriction to satisfy the equation of continuity, while its pressure must decrease due to conservation of energy; the gain in kinetic energy is supplied by a drop in pressure or a pressure gradient force.

The limiting case of the Venturi effect is choked flow, in which a constriction in a pipe or channel limits the total flow rate through the channel because the pressure cannot drop below zero in the constriction. Choked flow is used to control the delivery rate of water and other fluids through spigots and other types of valves. The portable apparatus of the present invention utilizes a source of pressurized medical fluid, to produce the desired pressure and flow for the effective creation of an enriched medical suspension.

SUMMARY

In one aspect a medical fluid suspension generating delivery apparatus includes a dual syringe assembly including a first receptacle for a pressurized chemical solution and a second receptacle for a medical solution. The medical fluid suspension generating delivery apparatus also includes a Venturi-agitating tip assembly generating an enriched medical suspension from the pressurized chemical solution and a second receptacle for a medical solution.

In some embodiments the dual syringe assembly includes a syringe body including a receptacle support having a first recess in which the first receptacle is mounted and a second recess in which the second receptable is mounted.

In some embodiments sizes of the first receptacle and the second receptacle are different.

In some embodiments the first and second receptacles are oriented parallel to each other such that outlets of the respective first and second receptacles are aligned for connection with respective input cannulas of a dual lumen catheter connecting the pressurized chemical solution and the medical solution to the Venturi-agitating tip assembly.

In some embodiments the first receptacle includes a cylindrical body with a first end shaped and dimensioned to receive a first plunger and a second end defining the outlet of the first receptacle, and the second receptacle includes a cylindrical body with a first end shaped and dimensioned to receive a second plunger and a second end defining the outlet of the second receptacle.

In some embodiments an actuation member engages the first and second plungers such that the first and second plungers are moved in a coordinated manner.

In some embodiments the actuation member and the first and second plungers are oriented such that upon actuation a small amount of the pressurized chemical solution flows through the Venturi-agitating tip assembly before the medical solution flows therethrough.

In some embodiments the actuation member is fixedly attached to the free end of the first plunger.

In some embodiments a controlled actuation assembly is oriented in alignment with the free end of the second plunger.

In some embodiments a cup at the free end of the second plunger fits about the second end the controlled actuation member. When the dual syringe assembly is filled and ready for use, the controlled actuation member is spaced from the free end of the second plunger, and when the thumb actuation member is first pressed downwardly only the first plunger is moved and the second plunger is not moved until the thumb actuation member has moved downwardly a distance sufficient to bring the second end of the controlled actuation member into contact with the free end of the second plunger.

Other objects and advantages of the present invention will become apparent from the following detailed description when viewed in conjunction with the accompanying drawings, which set forth certain embodiments of the invention.

BRIEF DESCRIPTION OF DRAWINGS

FIG. 1 is a perspective view of a dual syringe assembly prior to actuation.

FIG. 2 is a perspective view of the dual syringe assembly after use.

FIGS. 3, 4, and 5 are respectively a front elevation view, a top plan view, and a rear elevation view of the receptacle support.

FIG. 6 is a top plan view of the thumb actuation member.

FIG. 7 is a perspective view of the medical fluid suspension generating delivery apparatus.

FIGS. 8A, 8B, and 8C respectively show a longitudinal cross-sectional view, a perspective view and a perspective cross sectional view of a Venturi-agitating tip assembly in accordance with an alternate embodiment.

FIGS. 9A, 9B, 9C, and 9D are respectively a perspective view, a longitudinal cross-sectional perspective view, an exploded view and a lateral cross-sectional view of a Venturi-agitating tip assembly in accordance with an alternate embodiment.

FIGS. 10A, 10B, 10C, 10D, and 10E are respectively a perspective view, an exploded view, a front partial cross-sectional view, a rear partial cross-sectional view and a lateral cross-sectional view of a Venturi-agitating tip assembly in accordance with an alternate embodiment.

FIGS. 11A, 11B, 11C, 11D, 11E, and 11F are respectively a side elevation view, a detailed side elevation view, a detailed side elevation view, a perspective view, a longitudinal cross-sectional view, and a lateral cross-sectional view of a Venturi-agitating tip assembly in accordance with an alternate embodiment.

DETAILED DESCRIPTION

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to the various figures and embodiments, the medical fluid suspension generating delivery apparatus 100 for performing medical procedures includes a Venturi-agitating tip assembly (various embodiments of which are described below). Each of the Venturi-agitating tip assembly includes a multi-channel arrangement at a proximal first end thereof and a tip at a distal second end thereof. The delivery apparatus 100 also includes a dual syringe assembly 10 fluidly connected to the multi-channel arrangement at the proximal first end of the Venturi-agitating tip assembly. It is appreciate multiple embodiments of a Venturi-agitating tip assembly and the dual syringe assembly 10 is adapted work with any of the disclosed embodiments. In describing the dual syringe assembly 10 it is described with reference to the Venturi-agitating tip assembly 280 disclosed with reference to FIG. 7.

The dual syringe assembly 10 includes a first receptacle 12 for a pressurized chemical solution 14 and a second receptacle 16 for the medical solution 18. The pressurized chemical solution 14 and the medical solution 18 are combined within the Venturi-agitating tip assembly 280 in a manner generating an enriched medical suspension 20 that is ultimately dispensed from the suspension delivery apparatus 100. The enriched medical suspension 20 is then sprayed from the Venturi-agitating tip assembly 280. In accordance with a preferred embodiment, outlets 22 at the tip of the Venturi-agitating tip assembly 280 are oriented such that the enriched medical suspension 20 is sprayed at an angle of 25 degrees to 65 degrees, preferably 45 degrees, relative to the longitudinal axis of the Venturi-agitating tip assembly 280 to ensure the enriched medical suspension 20 is sprayed directly onto the inner wall of the lumen being treated and is not entrained within the fluid flowing in the lumen. This prevents the need for the application of the enriched medical suspension 20 down the middle of the lumen and waiting for the enriched medical suspension 20 to disperse out to the inner wall of the lumen. While the various embodiments disclosed below show the Venturi-agitating tip assembly with three (3) outlets, it is contemplated as many as 16 outlets may be positioned about the tip of the Venturi-agitating tip assembly for spraying the enriched medical suspension. Further still, it is appreciated the outlets may be covered with membranes enhancing delivery of the enriched medical suspension. A method in accordance with the apparatus is also disclosed.

With reference to FIGS. 1 to 6, the dual syringe assembly 10 is disclosed in detail. The dual syringe assembly 10 includes a syringe body 22 including a first receptacle 12 for a pressurized chemical solution 14 and a second receptacle 16 for the medical solution 18 for dispensing from outlets 24, 26 of the dual syringe assembly 10. Referring to FIGS. 1 to 5, the syringe body 22 includes a receptacle support 50 having a first recess 52 in which the first receptacle 12 is mounted and a second recess 54 in which the second receptable 16 is mounted. In accordance with a disclosed embodiment, the first and second receptacles 12, 16 are secured to the first and second recesses 52, 54 via adhesive, although it is appreciated the coupling could be achieved via a variety of known mechanisms.

The dual syringe assembly 10 therefore includes a cylindrical first receptable 12 and a cylindrical second receptacle 16. The first and second receptacles 12, 16 are oriented parallel to each other such that the outlets 24, 26 of the respective first and second receptacles 12, 16 are aligned for connection with respective input cannulas of the dual lumen catheter 260 connecting the pressurized chemical solution 14 and the medical solution 18 to the Venturi-agitating tip assembly 280.

The first receptacle 12 includes a cylindrical body 28 with a first end 28*a* shaped and dimensioned to receive a first plunger 30 and a second end 28*b* defining the outlet 24 of the first receptacle 12. The second receptacle 16 includes a cylindrical body 32 with a first end 32*a* shaped and dimensioned to receive a second plunger 34 and a second end 32*b* defining the outlet 26 of the second receptacle 16. As will be appreciated based upon the following disclosure relating to the operation of the delivery apparatus 100, the sizes of the first receptacle 12 and the second receptacle 16 are different to accommodate desired quantities of the pressurized chemical solution 14 and the medical solution 18 for passage through the Venturi-agitating tip assembly 280 and dispensing as disclosed below. With this in mind, the first receptacle 12 is sized to accommodate volumes from 2 ml to 60 ml, and the second receptacle 16 is sized to accommodate volumes from 2 ml to 20 ml. Each of the first outlet 24 and the second outlet 26 includes a one-way valve 36, 38 to ensure that the pressurized chemical solution 14 and the medical solution 18 only flows out of the dual syringe assembly 10.

Actuation of the first and second plungers 30, 34 is controlled by a single thumb actuation member 40 that is fixedly linked to the free end 30*f* of the first plunger 30 and contacts the second end 34*f* of the second plunger 34 via a controlled actuation member 42. The single thumb actuation member 40 engages the first and second plungers 30, 34 such that the first and second plungers 30, 34 are moved in a coordinated manner. Movement of the single thumb actuation member 40 is further controlled by a guide rod 43 that extends downwardly from the member thumb actuation member 40 and passes through an alignment recess 45 in the receptacle support 50. As will be appreciated based upon the following disclosure, and in accordance with a disclosed embodiment, the thumb actuation member 40 and the first and second plungers 30, 34 are oriented such that upon actuation a small amount of the pressurized chemical solution 14 flows through the Venturi-agitating tip assembly 280 before the medical solution 18 flows therethrough.

As discussed above, the thumb actuation member 40 is fixedly attached to the free end 30*f* of the first plunger 30. The thumb actuation member 40 includes a plate member 44 having an upper surface 44*u* shaped and dimensioned for engagement with the thumb of a user and a lower surface 441 coupled to the free end 30*f* of the first plunger 30. The controlled actuation member 42 also extends from the lower surface 441 of the plate member 44.

The controlled actuation member 42 is a cylindrical member with the first end 46 coupled to the lower surface 441 of the plate member 44 and the second end 48 facing and in alignment with the free end 34*f* of the second plunger 34 such that a cup 35 at the free end 34*f* of the second plunger 34 fits about the second end 48 of the controlled actuation member 42. However, and when the dual syringe assembly 10 is filled and ready for use, the controlled actuation member 42 is spaced from the free end 34*f* of the second plunger 34. As such, and when the thumb actuation member 40 is first pressed downwardly, only the first plunger 30 is moved. The second plunger 34 is not moved until the thumb actuation member 42 has moved downwardly a distance sufficient to bring the second end 48 of the controlled actuation member 42 into contact with the free end 34*f* of the second plunger 34. At this point both the first and second plungers 30, 34 are moved forcing the pressurized chemical solution 14 and the medical solution 18 out of the dual syringe assembly 10. Movement of the cup 35, and ultimately the second plunger 34, relative to the controlled actuation member 42 is limited by a radially extending ridge 48r at the second end 48 of the controlled actuation member 42 that interact with an inwardly extending ridge 35r at the open end of the cup 35.

Figure 7:
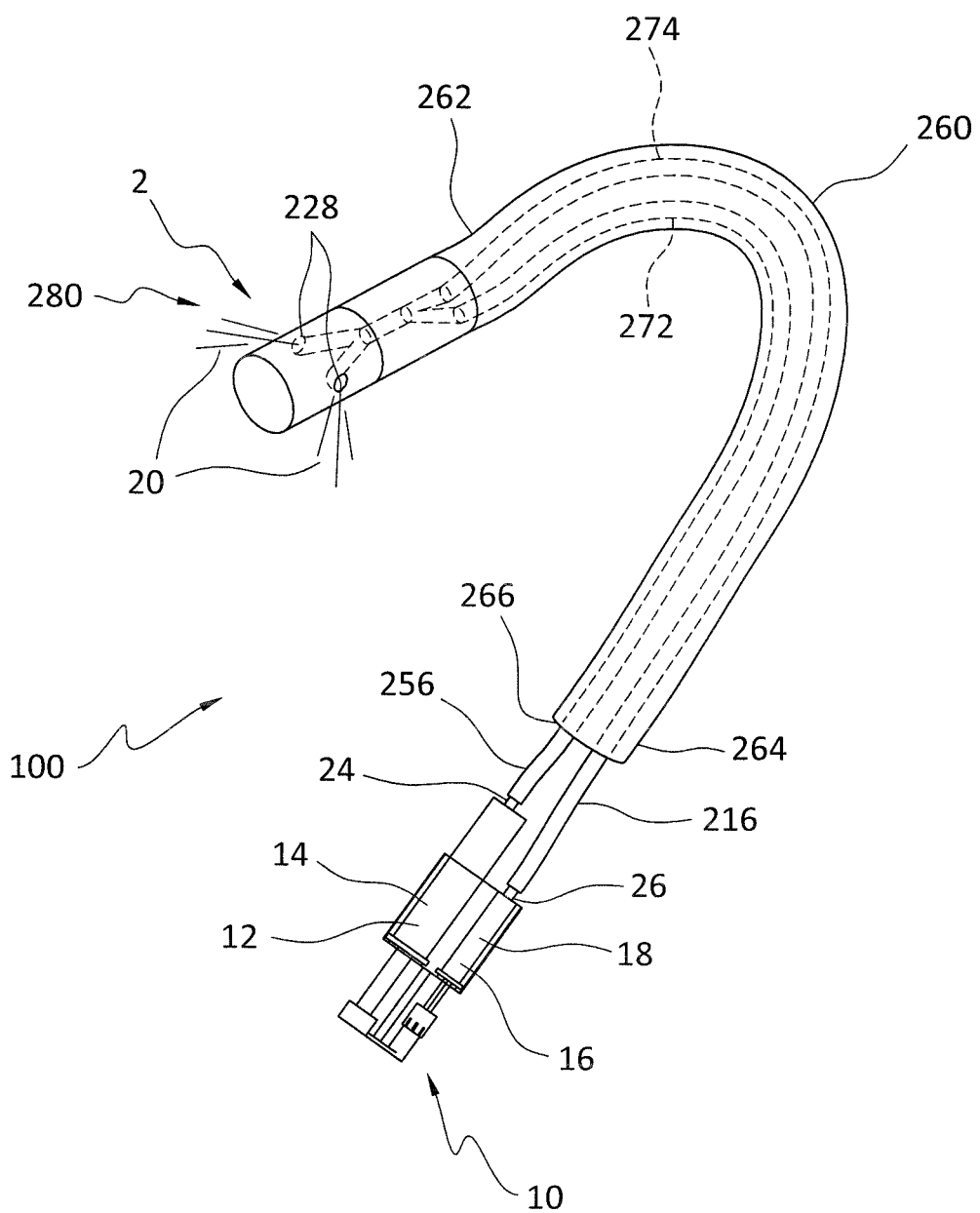

With reference to FIG. 7, the entire delivery apparatus 100 is shown. The suspension delivery catheter 2 includes a dual lumen catheter 260 connecting a Venturi-agitating tip assembly 280 to the pressurized chemical solution 14 and the medical solution 18 from the dual syringe assembly 10. As mentioned above, the dual syringe assembly 10 includes one-way valves at its outlets to ensure only flows out of the dual syringe assembly 10. The suspension delivery catheter 2 includes a first end (or distal end) 262 having the Venturi-agitating tip assembly 280 and a second end (or proximal end) 264 to which the dual syringe assembly 10 is fluidly connected for the passage of the pressurized chemical solution 14 and the medical solution 18. As will be appreciated based upon the following disclosure, the dual lumen catheter 260 is connected to the Venturi-agitating tip assembly 280 by securing the Venturi-agitating tip assembly 280 to a first lumen 272 and a second lumen 274 of the dual lumen catheter 260, respectively. The provision of the Venturi-agitating tip assembly 280 at the very end of the catheter allows for the mixing of the pressurized chemical solution 14 and the medical solution 18 immediately adjacent the discharge point.

A micro-hose 256 connects the dual syringe assembly 10 to the first lumen 272 of the dual lumen catheter 260 at a proximal first end 266 of the dual lumen catheter 260 for the transmission of the pressurized chemical solution 14 from dual syringe assembly 10 to the Venturi-agitating tip assembly 280. As such, pressurized chemical solution 14 leaving the dual syringe assembly 10 enters the first lumen 272 of the dual lumen catheter 260 via the micro-hose 256. After passing through the first lumen 272 of the dual lumen catheter 260, the pressurized medical chemical solution 14 enters the Venturi-agitating tip assembly 280 of the suspension delivery catheter 2. As will be explained below in greater detail, the medical suspension 20 composed of the chemical solution 14 and the medical solution 18 generated at the Venturi-agitating tip assembly 280 is directly applied to a vein or artery requiring treatment with the medical suspension 20.

As to the connection of the medical solution 18 to the suspension delivery catheter 2, the medical solution 18 is delivered to the second lumen 274 of the dual lumen catheter 260 at the proximal first end 266 thereof, and ultimately to the Venturi-agitating tip assembly 280, via a container, in particular, the syringe 290, connected to the second lumen 274 of the dual lumen catheter 260 by a supply line 216. As mentioned above, the dual syringe assembly 10 includes one-way valves at its outlets to ensure that the pressurized chemical solution 14 and the medical solution 18 from the dual syringe assembly 10 only flow out of the dual syringe assembly 10, preventing reflux back into the dual syringe assembly 10. After passing through the second lumen 274 of the dual lumen catheter 260, the medical solution 18 from the dual syringe assembly 10 travels into the Venturi-agitating tip assembly 280 where it is combined with pressurized chemical solution 14 from the dual syringe assembly 10 to form an enriched medical suspension 20.

The Venturi-agitating tip assembly 280 results in the spray of the enriched medical suspension 20 at an angle relative to a central axis of the Venturi-agitating tip assembly 280. In accordance with a preferred embodiment, and as will be discussed below with regard to the various embodiments of the Venturi-agitating tip assembly 280, the Venturi-agitating tip assembly 280 includes outlets 228 directing the enriched medical suspension 20 at an angle of 25 degrees to 65 degrees, preferably 45 degrees, relative to the central longitudinal axis of the Venturi-agitating tip assembly 280. By orienting the outlets at an angle as disclosed herein, the enriched medical suspension 20 is directed toward the walls of the vessel in which it is being dispensed.

It is appreciated various tip assemblies and enriched medical suspension generating structures may be employed in accordance with the present invention. In accordance with a first embodiment as shown with reference to FIGS. 8A-8C, the Venturi-agitating tip assembly 380 employs a Venturi arrangement with a mixing chamber 324. The Venturi-agitating tip assembly 380 has a proximal first end 380a and a distal second end 380b. The Venturi-agitating tip assembly 380 includes a hollow cylindrical elongated body 310 having a proximal first end 312, which coincides with the proximal first end 380a of the Venturi-agitating tip assembly 380, and a distal second end 314. The proximal first end 380a of the Venturi-agitating tip assembly 380 includes a multi-channel arrangement 381 including first and second inputs 316, 318 for attachment to the dual lumen catheter 360. The first and second inputs 316, 318 respectively lead to a first channel 320 and a second channel 322 of the multi-channel arrangement 381 of the Venturi-agitating tip assembly 380. The first and second channels 320, 322 lead to, and are in fluid communication with, a mixing chamber 324 (which also forms part of the multi-channel arrangement 381) located in the central portion 326 of the Venturi-agitating tip assembly 380, that is, between the proximal first end 380a and the distal second end 380b. Located at the distal second end 380b of the Venturi-agitating tip assembly 380, and secured to the distal second end 314 of the elongated body 310, is a spray tip 328 directing the enriched medical suspension in a spray pattern onto the inner lumen of a vessel.

The first channel 320 and the second channel 322 are interconnected in a manner creating a Venturi effect causing the pressurized chemical solution to effectively pull the medical solution through the second channel 322 and into the mixing chamber 324. This is achieved by providing with the first channel 320 with a reduced diameter as it extends from the proximal first end 312 of the elongated body 310 (that is, the first end 320a of the first channel 320) to the central portion 326 of the Venturi-agitating tip assembly 380 (that is, the second end 320b of the first channel 320). In accordance with a preferred embodiment, the diameter of the first channel 320 decreases from a diameter of 0.038 inches adjacent the proximal first end 312 of the elongated body 310 to a diameter of 0.017 inches adjacent the mixing chamber 324.

As mentioned above, the second channel 322 is in fluid communication with the first channel 320. This is achieved by the provisional of a transverse channel 330 connecting the second end 320b of the first channel 320 with the second end 322b of the second channel 322. In particular, the second channel 322 includes a first end 322a adjacent the proximal first end 312 of the elongated body 310 and a second end 322b adjacent the mixing chamber 324 (although not directly in fluid communication with the mixing chamber 324) and the transverse channel 330. In accordance with a preferred embodiment, the diameter of the second channel 322 is 0.031 inches and remains consistent as it extends from the first end 322a thereof to the second end 322b thereof.

The first lumen 372 of the dual lumen catheter 360 supplies the pressurized chemical solution and the second lumen 374 supplies the medical solution. It is, however, appreciated the functions of the first and second lumens could be flipped in this embodiment as well as other embodiments. As such, the first lumen 372 is connected to, and in fluid communication with, the first channel 320 of the Venturi-agitating tip assembly 380 and the second lumen 374 is connected to, and in fluid communication with, the second channel 322 of the Venturi-agitating tip assembly 380. In practice, the medical solution from the dual syringe assembly 10 travels through the second lumen 374 of the dual lumen catheter 360 and into the second channel 322 when pressurized chemical solution enters the first channel 320 and passes the transverse channel 330 as it flows into the mixing chamber 324 after being actuated and released from the dual syringe assembly 10. The pressurized chemical solution entering, and passing through, the Venturi-agitating tip assembly 380 imparts negative pressure on the medical solution in the dual syringe assembly 10 and draws the medical solution from the dual syringe assembly 10 through the second channel 322, through the second lumen 374 of the dual lumen catheter 360, through the transverse channel 330, and into the mixing chamber 324 due to the Venturi effect. The medical solution and the pressurized chemical solution are then mixed within the mixing chamber 324 to form an enriched medical suspension. The second plunger 30 is used to regulate or stop flow of medical solution of chemical solution from the dual syringe assembly 10.

The pressurized chemical solution and medical solution mixing in the mixing chamber 324 are then forced through the spray tip 328 from which the enriched medical suspension is sprayed upon the inner lumen of a vessel. The spray tip 328 includes a plurality of outlets 328a oriented at an angle of 25 degrees to 65 degrees, preferably 45 degrees, relative to the central longitudinal axis of the Venturi-agitating tip assembly 380. The force of the pressurized chemical solution traveling through the Venturi-agitating tip assembly 380 and exiting through the spray tip 328 as part of an enriched medical suspension projects the enriched medical suspension from the distal second end 384 of the Venturi-agitating tip assembly 380 as a spray and onto the inner lumen of a vessel.

In accordance with a second embodiment as shown with reference to FIGS. 9A to 9D, a Venturi-agitating tip assembly 480 employs a spray tip 428 in conjunction with a multi-channel arrangement 481 where the pressurized chemical solution and medical solution are mixed and forced through the spray tip 428. The Venturi-agitating tip assembly 480 includes a proximal first end 480a and a distal second end 480b. The Venturi-agitating tip assembly 480 includes a hollow cylindrical elongated body 410 having a proximal first end 412, which coincides with the proximal first end 480a of the Venturi-agitating tip assembly 480, and a distal second end 414. The Venturi-agitating tip assembly 480 is adapted for use with a dual lumen catheter 460, in particular a dual lumen catheter having concentric lumens, wherein the outer first lumen 472 is annular shaped for the passage of pressurized chemical solution (and has an outer diameter of 0.092 inches at the outer wall thereof and an inner diameter of 0.042 inches at the inner wall thereof) and the inner second lumen 474 is circular shaped for the passage of the medical solution (and has a diameter of 0.030 inches). The inner second lumen 474 is supported within the outer first lumen 472 by first and second radially extending rib members 473a, 473b (each having a thickness of 0.006 inches) that extend from the outer surface of the second lumen 474 to the inner surface of the outer first lumen 472. In this way the outer first lumen 472 is divided into first and second semicircular passageways 475a, 475b.

Figure 9D:
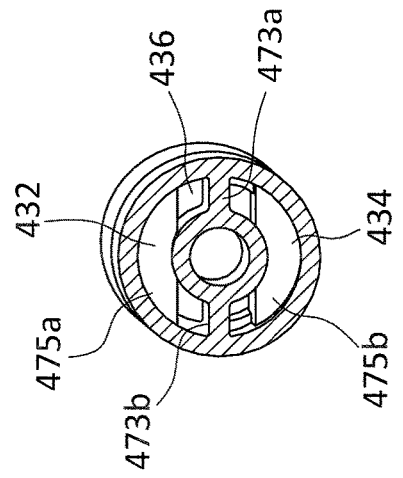
Figure 9C:
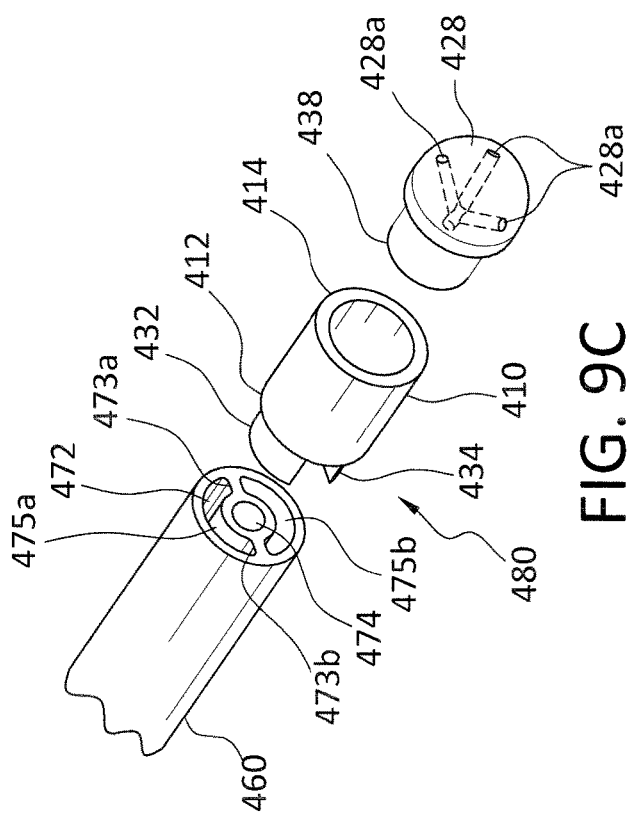
Figure 9A:
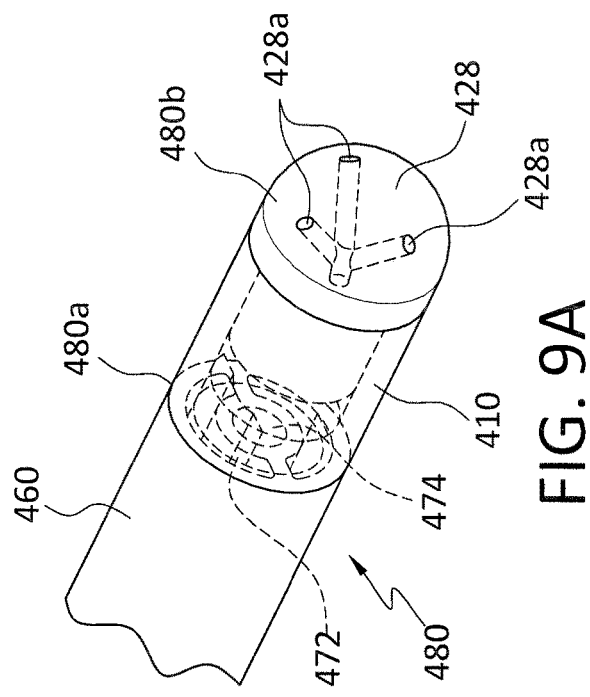
Figure 9B:
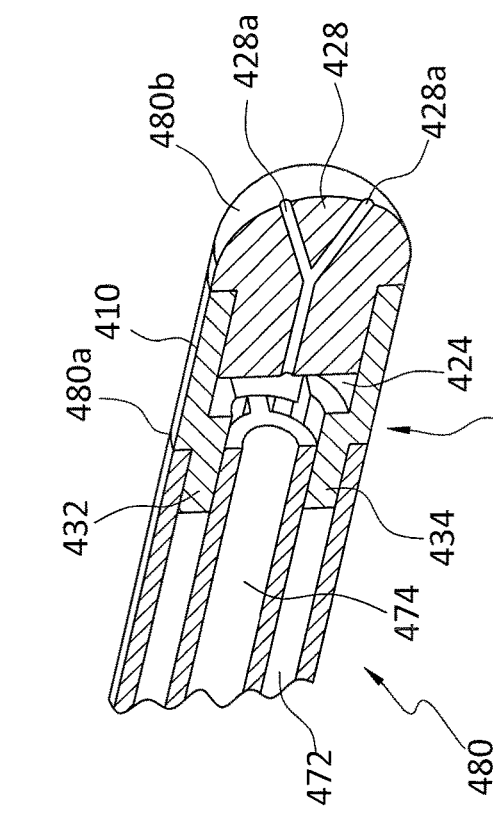
Figure 10C:
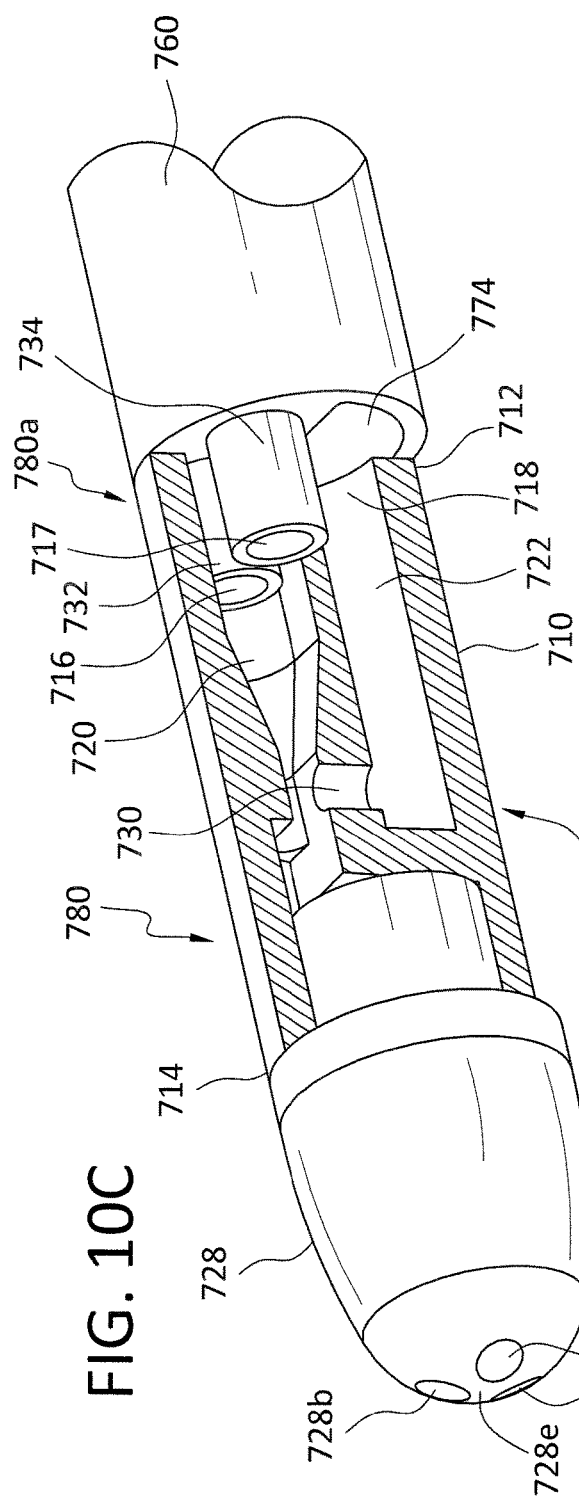
Figure 10D:
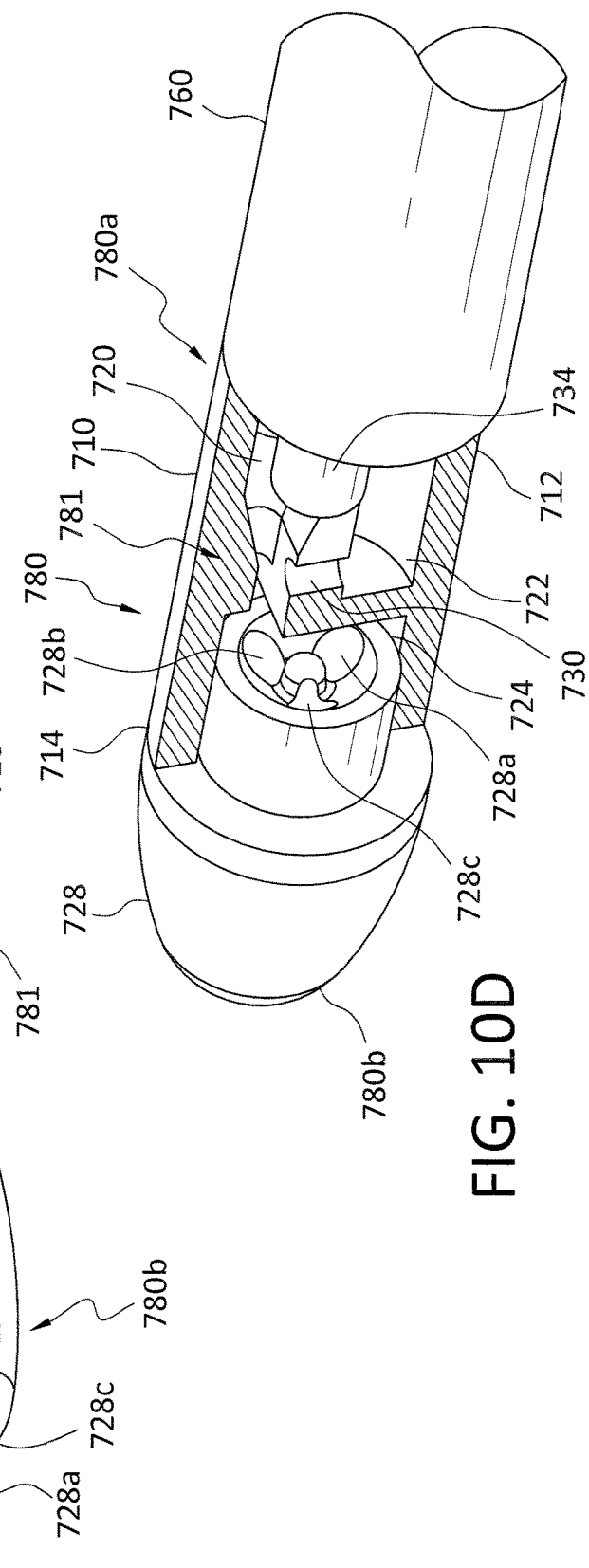
Figure 10E:
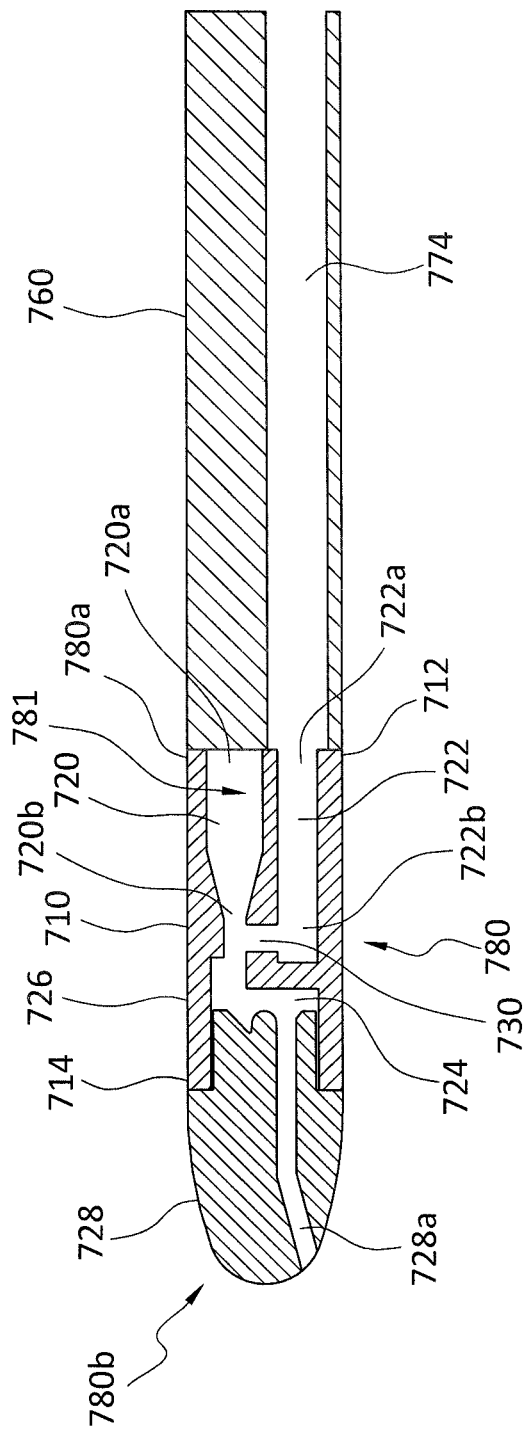
Figure 11A:
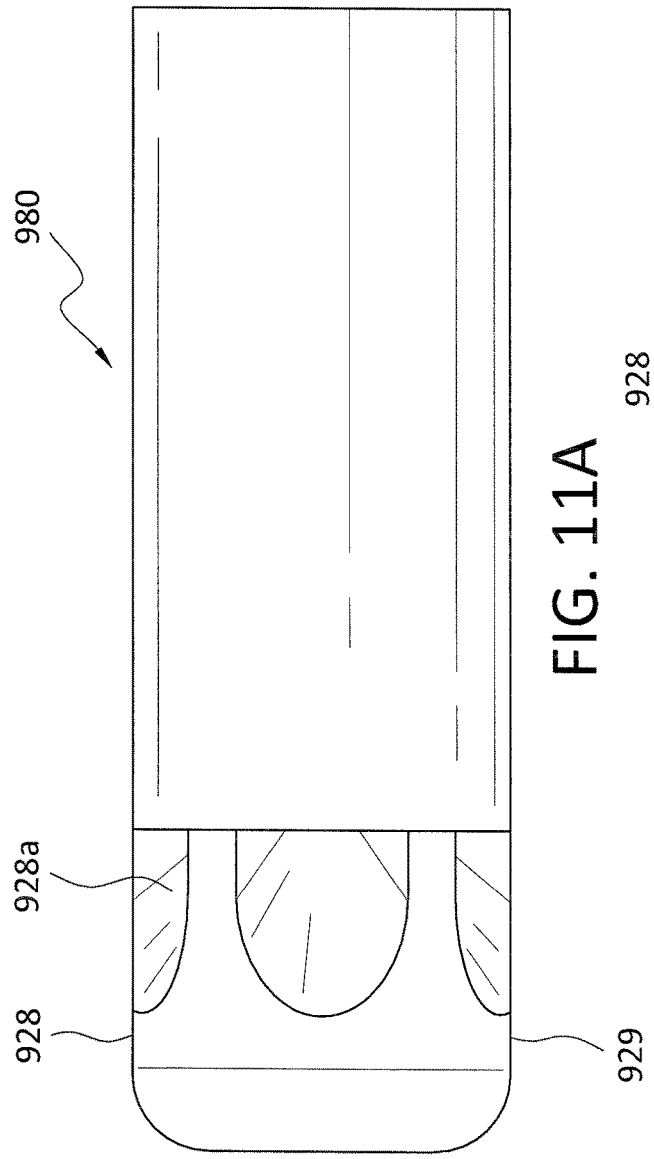
Figure 11B:
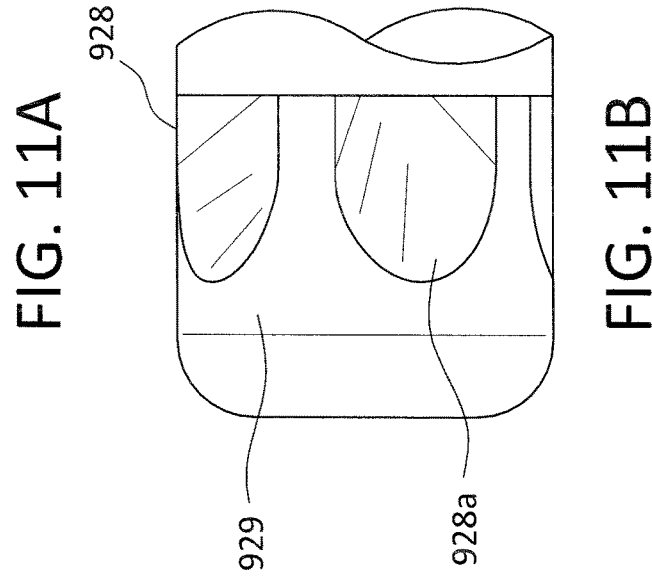
Figure 11E:
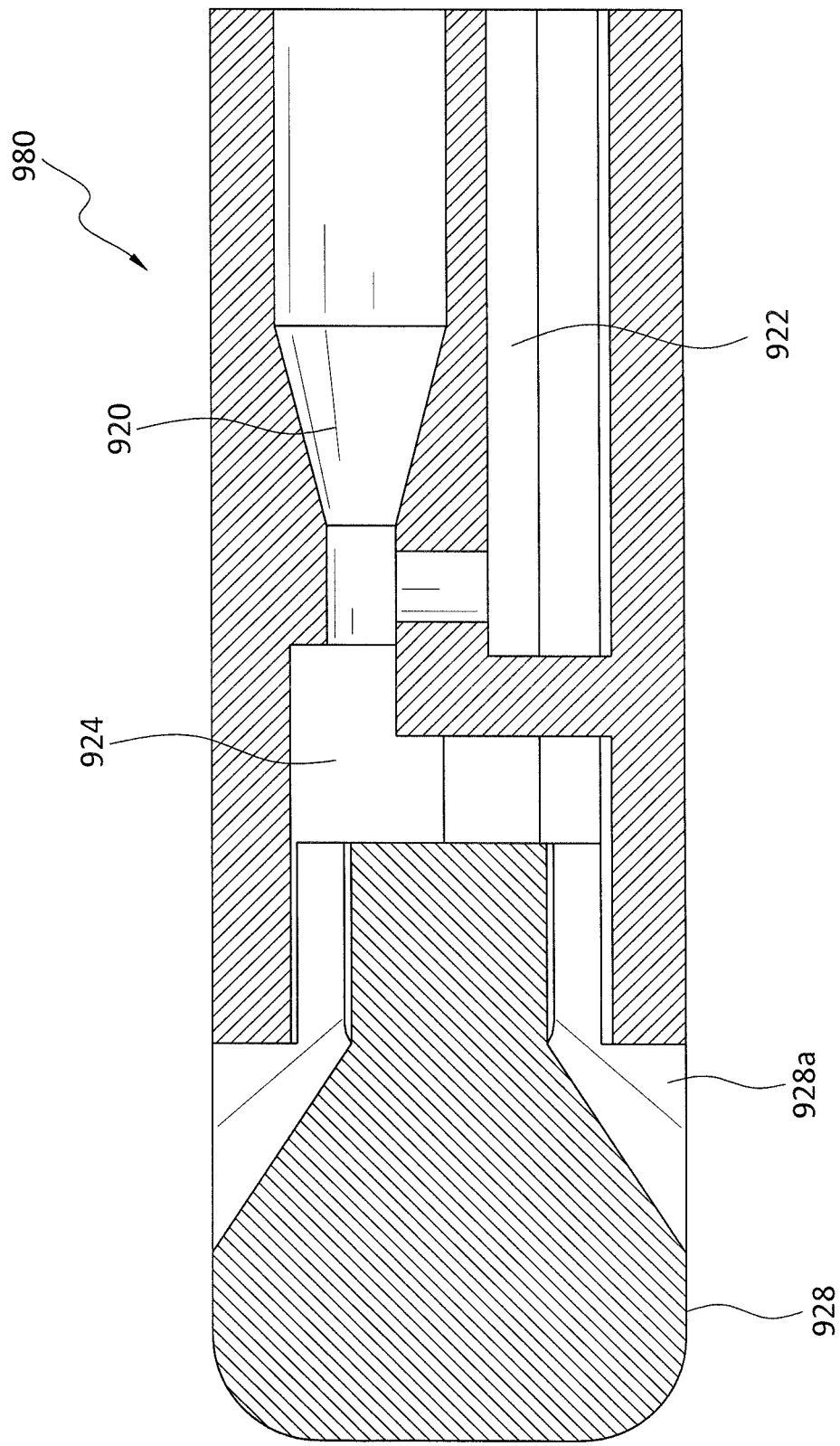
Figure 11F:
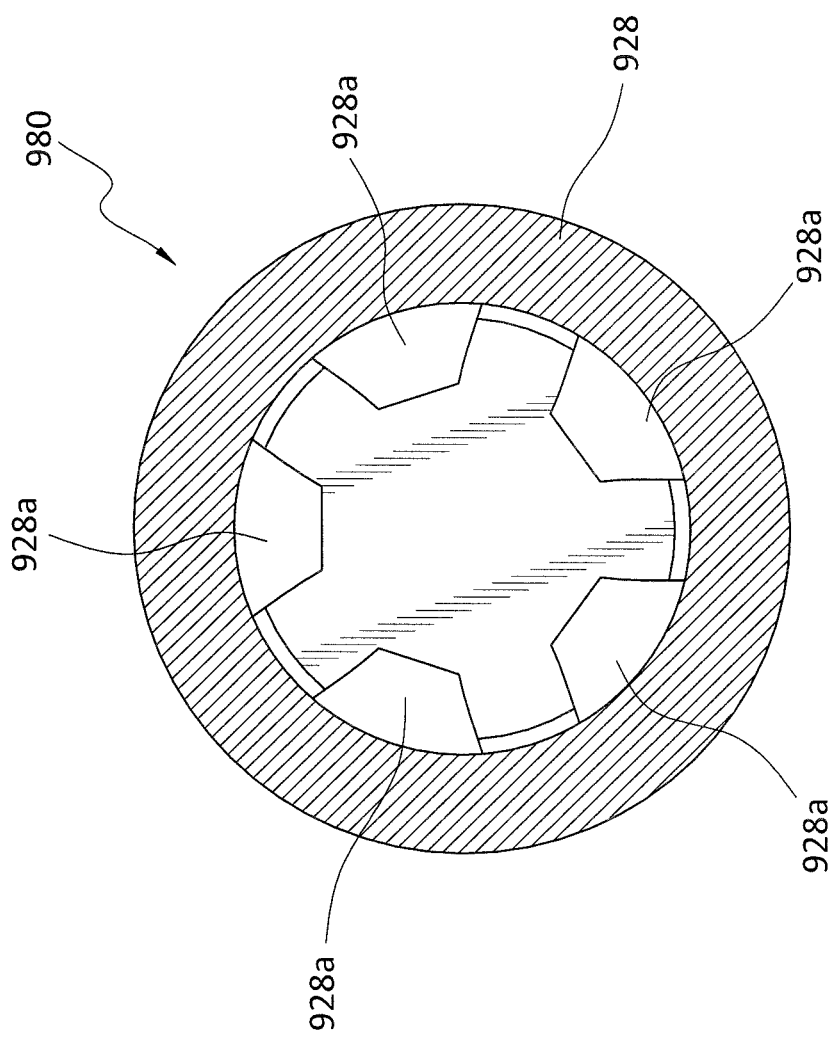

The proximal first end 480a of the Venturi-agitating tip assembly 480, in particular, the proximal first end 412 of the elongated body 410 is formed with two projections 432, 434 shaped and dimensioned for engagement within the outer first lumen 472 of the catheter 460 in a manner blocking a substantial portion of the outer first lumen 472. The two projections 432, 434 are arcuate members shaped and dimensioned to respectively block substantial portions of the first and second semicircular passageways 475a, 475b while creating four small passageways 436, each of approximately 0.031 inches (along the Y-axis as shown in FIG. 9D) by 0.050 inches (along the X-axis as shown in FIG. 9D) for the passage of pressurized chemical solution therethrough. The four small passageways 436 are defined by spaces existing between the edges of the arcuate members 432, 434 and the first and second radially extending rib members 473a, 473b.

The remainder of the Venturi-agitating tip assembly 480 includes a central mixing chamber 424 that is in fluid communication with the second lumen 474 and the four small passageways 436 feeding pressurized chemical solution from the first lumen 472. Secured to, and closing off, the second end 414 of the elongated body 410 is a spray tip 428, which is thereby at the distal second end 480b of the Venturi-agitating tip assembly 480. Attachment of the spray tip 428 to the elongated body 410 is achieved by providing the spray tip 428 with a projection 438 that seats within the opening at the second end 414 of the elongated body 410.

The first lumen 472 and the second lumen 474 are interconnected in a manner causing the pressurized chemical solution to effectively pull the medical solution through the second lumen 474 and into the mixing chamber 424. In practice, the medical solution from the dual syringe assembly 10 travels through the second lumen 474 of the dual lumen catheter 460 and into the mixing chamber 424 when pressurized chemical solution passes through the four small passageways 436 and enters the mixing chamber 424 (where the medical solution from the syringe 290 and the pressurized chemical solution mix to form an enriched medical suspension) after being actuated and released from dual syringe assembly 10. The pressurized chemical solution entering, and passing through, the mixing chamber 424 imparts negative pressure on the medical solution in dual syringe assembly 10 and draws the medical solution from the dual syringe assembly 10 through the second lumen 474 and into the mixing chamber 424. The second plunger 30 is used to regulate or stop flow of the medical solution from the dual syringe assembly 10.

The pressurized chemical solution and medical solution mixing in the mixing chamber 424 are then forced through the spray tip 428 from which an enriched medical suspension is sprayed upon the inner surface of a lumen. The spray tip 428 includes a plurality of outlets 428a oriented at an angle of 25 degrees to 65 degrees, preferably 45 degrees, relative to the central longitudinal axis of the Venturi-agitating tip assembly 480. The force of the pressurized chemical solution traveling through the Venturi-agitating tip assembly 480 and exiting through the spray tip 428 as part of an enriched medical suspension projects the enriched medical suspension from the distal second end 484 of the Venturi-agitating tip assembly 480 as a spray and onto the inner lumen of a vessel.

In accordance with a third embodiment as shown with reference to FIGS. 10A to 10E, a Venturi-agitating tip assembly 780 employs a tip 728 in conjunction with a multi-channel arrangement 781 where the pressurized chemical solution and medical solution are mixed to form an enriched medical suspension and forced through the tip 728. The Venturi-agitating tip assembly 780 includes proximal first end 780a and a distal second end 780b. The Venturi-agitating tip assembly 780 includes a hollow cylindrical elongated body 710 having a proximal first end 712, which coincides with the proximal first end 780a of the Venturi-agitating tip assembly 780, and a distal second end 714. The Venturi-agitating tip assembly 780 is adapted for use with a multi-lumen catheter 760, in particular a triple lumen catheter having parallel lumens, wherein the first and second lumens 772, 773 are circular shaped (each with a diameter of 0.039 inches) and are dimensioned for the passage of pressurized chemical solution and the third lumen 774 is semi-circular shaped (with a radius of 0.047 inches) and is dimensioned for the passage of the medical solution.

The proximal first end 712 of the elongated body 710 at the proximal first end 780a of the Venturi-agitating tip assembly 780 includes first, second and third inputs 716, 717, 718 for attachment to the multi-lumen catheter 760. The first and second inputs 716, 717 lead to a first channel 720 and the third input 718 to a second channel 722. As such, the proximal first end 712 of the elongated body 710 at the proximal first end 780a of the Venturi-agitating tip assembly 780 is formed with two circular tubular projections 732, 734, defining the first and second inputs 716, 717. The circular tubular projections 732, 734 (each with an inner diameter of 0.027 inches and an outer diameter of 0.039 inches) are shaped and dimensioned for engagement within the first and second lumens 772, 773 of the catheter 760 in a manner allowing for the flow of fluid from the first and second lumens 772, 773 and into the Venturi-agitating tip assembly 780. The two circular tubular projections 732, 734 are shaped and dimensioned to fit within the first and second lumens 772, 773 while maintaining passageways for the passage of pressurized chemical solution therethrough.

The first and second channels 720, 722 lead to, and are in fluid communication with, a mixing chamber 724 located in the central portion 726 of the Venturi-agitating tip assembly 780, that is, between the proximal first end 712 and the distal second end 714 of the elongated body. Secured to the distal second end 714 of the elongated body 710, and positioned at the distal second end 780b of the Venturi-agitating tip assembly 78, is a tip 728 having three outlets 728a, 728b, 728c extending from the mixing chamber 724 to the exterior at the distal end of the Venturi-agitating tip assembly 780 at an angle of 25 degrees to 65 degrees, preferably 45 degrees, relative to the central longitudinal axis of the Venturi-agitating tip assembly 780.

The first channel 720 and the second channel 722 are interconnected in a manner creating a Venturi effect causing the pressurized chemical solution to effectively pull the medical solution through the second channel 722 and into the mixing chamber 724. This is achieved by providing the first channel 720 with a reduced diameter (decreasing from 0.038 inches to 0.017 inches) as it extends from the proximal first end 712 of the elongated body 710 (that is, the first end 720a of the first channel 720) to the central portion 726 of the Venturi-agitating tip assembly 780 (that is, the second end 720b of the first channel 720). In accordance with a preferred embodiment, the diameter of the first channel 720 decreases from a diameter of 0.038 inches adjacent the proximal first end 712 of the elongated body 710 to a diameter of 0.017 inches adjacent the mixing chamber 724.

As mentioned above, the second channel 722 is in fluid communication with the first channel 720. This is achieved by the provisional of a transverse channel 730 connecting the second end 720b of the first channel 720 with the second end 722b of the second channel 722. In particular, the second channel 722 includes a first end 722a adjacent the proximal first end 712 of the elongated body 710 and a second end 722b adjacent the mixing chamber 724 (although not directly in fluid communication with the mixing chamber 724) and the transverse channel 730. In accordance with a preferred embodiment, the diameter of the second channel 722 is 0.047 inches and remains consistent as it extends from the first end 722a thereof to the second end 722b thereof.

The first and second lumens 772, 773 supply the pressurized chemical solution and the third lumen 774 supplies the medical solution. As such, the first and second lumens 772, 773 are connected to, and in fluid communication with, the first channel 720 of the Venturi-agitating tip assembly 780. The third lumen 774 is connected to, and in fluid communication with, the second channel 722 of the Venturi-agitating tip assembly 780. In practice, the medical solution from dual syringe assembly 10 travels through third lumen 774 of multi-lumen lumen catheter 760 and into the second channel 722 when pressurized chemical solution enters the first channel 720 and passes the transverse channel 730 (having a size of 0.020 inches) into the mixing chamber 724 after being actuated and released from dual syringe assembly 10. The pressurized chemical solution entering, and passing through, the Venturi-agitating tip assembly 780 imparts negative pressure on the medical solution in dual syringe assembly 10 and draws the medical solution from the dual syringe assembly 10 through second channel 722, through the third lumen 774 of the dual lumen catheter 760, and into the mixing chamber 724 due to the Venturi effect. The second plunger 30 is used to regulate or stop flow of medical solution from the dual syringe assembly 10.

The pressurized chemical solution and medical solution mixing in the mixing chamber 724 form an enriched medical suspension that is then forced through the outlets 728a-c of the spray tip 728. The force of the pressurized medical chemical solution traveling through the Venturi-agitating tip assembly 780 and exiting through the spray tip 728 as part of an enriched medical suspension projects the enriched medical suspension from the distal second end 784 of the Venturi-agitating tip assembly 780 as a spray and onto the inner lumen of a vessel.

While the outlets of the spray tip in the embodiments disclosed above with reference to FIGS. 8A-C, FIGS. 9A-D, and 10A-E are positioned along a forward portion of the spray tip, it is appreciated the outlets of the spray tip could be positioned along the outer circumferential wall of the spray tip as shown in FIG. 7. Through the utilization of either position for the outlets, the enriched medical suspension is sprayed from the Venturi-agitating tip assembly onto the inner lumen of a vessel.

For example, and with reference to FIG. 11A-11F, a fourth embodiment with outlets 928a of the spray tip 928 positioned along the outer circumferential wall 929 of the spray tip 928. Those portions of the Venturi-agitating tip assembly 980 proximal to the spray tip 928, for example, the mixing chamber 924, the first channel 920, and the second channel 922 are the same as found in the embodiment disclosed with reference to FIGS. 8A to 8C. However, the spray tip 928 includes a plurality of circumferentially oriented outlets 928a positioned so as to dispense the enriched medical suspension through the outer circumferential wall 929 of the spray tip 928.

In accordance with the various embodiments described above, the enriched medical suspension exiting the Venturi-agitating tip assembly is directed to a vessel requiring treatment. In accordance with a preferred embodiment, the method for treatment in accordance with the present invention is achieved in the following manner. The first end of the suspension delivery catheter, that is, Venturi-agitating tip assembly is introduced into a diseased/varicosed vein requiring treatment such that the first end of Venturi-agitating tip assembly is positioned beyond the section of vein requiring treatment. The second end of the delivery catheter is coupled to the compressed medical fluid unit and the syringe. At this point, the compressed medical fluid unit is actuated to supply pressurized chemical solution to the suspension delivery catheter and an enriched medical suspension is produced at the Venturi-agitating tip assembly of the suspension delivery catheter. The enriched medical suspension sprays from the first end of Venturi-agitating tip assembly into the section of vein, artery, or other vessel requiring treatment. For example, and where the enriched medical suspension includes a sclerosant for the destruction of a diseased vein, as the catheter is withdrawn from the vein, the enriched medical suspension is sprayed into the vein at various segments causing the vein to go into spasm resulting in eventual destruction of the diseased vein. Where the present invention is used in the treatment of the arterial or venous system without the goal of spasm or vessel destruction, the enriched medical suspension is sprayed, or otherwise delivered, as required for the procedure being performed.

It is appreciated this procedure can be performed under ultrasound guidance or radiograph in order for the physician to control the amount of liquid to mix with the pressurized chemical solution to form the enriched medical suspension.

In addition to the treatment of diseased veins as discussed above, the present suspension delivery catheter may be used in the treatment of various vascular ailments. The potential treatments that may employ the present suspension delivery catheter include, but are not limited to the following, oncology medical solutions, microbeads, magnetic beads, or particles for thrombus treatment, metallic beads, or particles for thrombus treatment, embolics, driving drugs through the blood-brain barrier for neurological conditions, driving or delivering TPA (Tissue Plasminogen Activator) for thrombolytic usage, etc.

It is appreciated that where microparticles are used in conjunction with the enriched medical suspension composed of the chemical and medical solutions, saline may be used with the microparticles, so as to place the microparticles into suspension.

While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

While the preferred embodiments have been shown and described, it will be understood that there is no intent to limit the invention by such disclosure, but rather, it is intended to cover all modifications and alternative constructions falling within the spirit and scope of the invention.

The invention claimed is:

1. A medical fluid suspension generating delivery apparatus, comprising:
   a dual syringe assembly including a first receptacle for a pressurized chemical solution and a second receptacle for a medical solution, the first receptacle includes a cylindrical body with a first end shaped and dimensioned to receive a first plunger and a second end defining an outlet of the first receptacle, and the second receptacle includes a cylindrical body with a first end shaped and dimensioned to receive a second plunger and a second end defining an outlet of the second receptacle,
   the dual syringe assembly further including an actuation member engaging the first and second plungers such that the first and second plungers are moved in a coordinated manner, the actuation member comprising a controlled actuation assembly oriented in alignment with a free end of the second plunger; and
   a Venturi-agitating tip assembly generating an enriched medical suspension from the pressurized chemical solution and the medical solution;
   wherein when the dual syringe assembly is filled and ready for use, the controlled actuation assembly is spaced from the free end of the second plunger, and when the actuation member is first pressed downwardly only the first plunger is moved and the second plunger is not moved until the actuation member has moved downwardly a distance sufficient to bring a second end of the controlled actuation assembly into contact with the free end of the second plunger.

2. The medical fluid suspension generating delivery apparatus according to claim 1, wherein the dual syringe assembly includes a syringe body including a receptacle support having a first recess in which the first receptacle is mounted and a second recess in which the second receptacle is mounted.

3. The medical fluid suspension generating delivery apparatus according to claim 1, wherein sizes of the first receptacle and the second receptacle are different.

4. The medical fluid suspension generating delivery apparatus according to claim 1, wherein the first and second receptacles are oriented parallel to each other such that the outlets of the respective first and second receptacles are aligned for connection with respective input cannulas of a dual lumen catheter connecting the pressurized chemical solution and the medical solution to the Venturi-agitating tip assembly.

5. The medical fluid suspension generating delivery apparatus according to claim 1, wherein the actuation member and the first and second plungers are oriented such that upon actuation a small amount the pressurized chemical solution flows through the Venturi-agitating tip assembly before the medical solution flows therethrough.

6. The medical fluid suspension generating delivery apparatus according to claim 5, wherein the actuation member is fixedly attached to a free end of the first plunger.

7. The medical fluid suspension generating delivery apparatus according to claim 1, wherein a cup at the free end of the second plunger fits about the second end of the controlled actuation assembly.

8. A medical fluid suspension generating delivery apparatus, comprising:
   a dual syringe assembly comprising:

a first receptacle for a pressurized chemical solution and a second receptacle for a medical solution, the first receptacle includes a cylindrical body with a first end shaped and dimensioned to receive a first plunger and a second end defining an outlet of the first receptacle, and the second receptacle includes a cylindrical body with a first end shaped and dimensioned to receive a second plunger and a second end defining an outlet of the second receptacle;

the first and second receptacles are oriented parallel to each other such that the outlets of the respective first and second receptacles are aligned for connection with respective input cannulas of a dual lumen catheter connecting the pressurized chemical solution and the medical solution to a Venturi-agitating tip assembly;

the dual syringe assembly further including an actuation member engages the first and second plungers such that the first and second plungers are moved in a coordinated manner, the actuation member is fixedly attached to a free end of the first plunger and the actuation member includes a controlled actuation assembly is oriented in alignment with a free end of the second plunger;

the Venturi-agitating tip assembly generating an enriched medical suspension from the pressurized chemical solution and the medical solution;

wherein the actuation member and the first and second plungers are oriented such that upon actuation a small amount the pressurized chemical solution flows through the Venturi-agitating tip assembly before the medical solution flows therethrough and a cup at the free end of the second plunger fits about a second end of the controlled actuation assembly, wherein when the dual syringe assembly is filled and ready for use, the controlled actuation assembly is spaced from the free end of the second plunger, and when the actuation member is first pressed downwardly only the first plunger is moved and the second plunger is not moved until the actuation member has moved downwardly a distance sufficient to bring the second end of the controlled actuation assembly into contact with the free end of the second plunger.

* * * * *